United States Patent
Li et al.

(10) Patent No.: US 6,231,879 B1
(45) Date of Patent: May 15, 2001

(54) BIOCOMPATIBLE DEVICES WITH FOAM SCAFFOLDS

(75) Inventors: Rebecca Li, Needham, MA (US); Tyrone F. Hazlett, Coventry, RI (US)

(73) Assignee: Neurotech S.A., Evry (FR)

( * ) Notice: Subject to any disclaimer, the term of this patent is extended or adjusted under 35 U.S.C. 154(b) by 0 days.

(21) Appl. No.: 09/230,506

(22) PCT Filed: Jul. 31, 1997

(86) PCT No.: PCT/US97/13541

§ 371 Date: Feb. 9, 1999

§ 102(e) Date: Feb. 9, 1999

(87) PCT Pub. No.: WO98/05304

PCT Pub. Date: Feb. 12, 1998

Related U.S. Application Data (63) Continuation of application No. 08/690,969, filed on Aug. 1, 1996, now Pat. No. 6,054,142.

(51) Int. Cl.$^7$ .................................................. A61K 9/00
(52) U.S. Cl. ....................... 424/422; 424/533; 424/534; 424/548; 424/549; 424/550; 424/557; 424/562; 424/569; 424/570; 424/572; 424/574; 424/577; 523/105; 523/112; 523/113; 523/122; 523/200; 523/218; 524/9; 524/10; 524/17; 524/20; 524/21; 524/1
(58) Field of Search .................... 523/122, 112, 523/113, 114, 200, 201, 205, 218; 524/1, 9, 10, 17, 20, 21; 424/422, 533–534, 548–551, 553, 556–572, 574, 577–580

(56) References Cited

U.S. PATENT DOCUMENTS

| | | |
|---|---|---|
| 2,609,347 | 9/1952 | Wilson . |
| 3,106,483 * | 10/1963 | Kline ..................................... 424/423 |
| 4,892,538 | 1/1990 | Aebischer et al. . |
| 4,920,203 * | 4/1990 | Tang et al. ............................ 525/409 |
| 4,921,703 | 5/1990 | Higuchi et al. . |
| 4,968,733 | 11/1990 | Muller et al. . |
| 4,976,859 | 12/1990 | Wechs . |
| 5,158,881 | 10/1992 | Aebischer et al. . |
| 5,283,187 | 2/1994 | Aebischer et al. . |
| 5,284,761 | 2/1994 | Aebischer et al. . |
| 5,464,440 | 11/1995 | Johansson . |
| 5,487,739 | 1/1996 | Aebischer et al. . |
| 5,550,050 | 8/1996 | Holland et al. . |
| 5,656,481 | 8/1997 | Baetge et al. . |
| 6,054,142 * | 4/2000 | Li et al. ................................ 424/426 |
| 6,071,530 * | 6/2000 | Polson et al. ........................ 424/426 |

FOREIGN PATENT DOCUMENTS

| | | |
|---|---|---|
| WO 91/00119 | 1/1991 | (WO) . |
| WO 92/19195 | 11/1992 | (WO) . |
| WO 93/00128 | 1/1993 | (WO) . |
| WO 95/01203 | 1/1995 | (WO) . |
| WO 95/05452 | 2/1995 | (WO) . |
| WO 96/02646 A2 | 2/1996 | (WO) . |

OTHER PUBLICATIONS

Kydonieus, Ed. CRC pp. 15, 132–134 1982 Insect suppression with controlled release pheromone systems.
Baetge et al., PNAS 83: 5454–5458 (1986).
Baron–Van Evercooren et al., Dev. Neurosci 8: 182–196 (1986).

(List continued on next page.)

*Primary Examiner*—Neil S. Levy
(74) *Attorney, Agent, or Firm*—Mintz, Levin, Cohn, Ferris, Glovsky and Popeo, P.C.

(57) ABSTRACT

This invention is directed to methods of manufacturing implantable biocompatible cell encapsulation devices, wherein the cell encapsulation devices have a jacket made of a permeable, biocompatible material that is loaded with a core made of a reticulate foam scaffold having interconnected pores, with cells that are dispersed in the interconnected pores.

8 Claims, 4 Drawing Sheets

OTHER PUBLICATIONS

Cabasso, Encyclopedia of Chemical Technology 12: 492–517 (1980).

Colton et al., the Kidney, eds., Brenner BM and Rector FC, pp. 2425–2489 (1981).

Dionne et al., ASAIO Abstracts, p. 99 (1993).

Hasirci, "Polyurethanes" in High Performance Biomaterials: A Comprehensive Guide to Medical and Pharmaceutical Applications, ed.,Szycher, pp. 71–89, Techomic Publishing, Lancaster, PA (1991).

Ray et al., PNAS 90: 3602–3606 (1993).

Richards et al., PNAS 89: 8591–8595 (1992).

Southern et al., J. Mol. Appl. Genet. 1:327 (1982).

Southern, P.J., In Vitro 18: 315 (1981).

* cited by examiner

FIG. 4 ically, the present invention provides a new biocompatible cell device with an internal foam scaffold.

BIOCOMPATIBLE DEVICES WITH FOAM SCAFFOLDS

This application is a 371 of PCT/US/97/13541, filed Jul. 31, 1947, and a continuation of Ser. No. 08/690,969 filed Aug. 1, 1996, now U.S. Pat. No. 6,054,142.

TECHNICAL FIELD OF THE INVENTION

This invention relates to biocompatible devices with foam scaffolds and to methods for making and using such devices.

BACKGROUND OF THE INVENTION

This invention relates to implantable encapsulation devices for the treatment of diseases and disorders with encapsulated cells or substances such as neurotransmitters, neuromodulators, hormones, trophic factors, growth factors, analgesics, enzymes, antibodies or other biologically active molecules. In particular, the invention relates to internally-supported, biocompatible cell encapsulation devices.

One encapsulation approach has been macroencapsulation, which typically involves loading living cells into hollow fiber (or other suitable shape) devices and then sealing the extremities. The encapsulation of such cells by a selectively permeable, or "permselective", membrane permits diffusion of the biological factors produced and secreted by the cells yet restrains the cells within a specific location. Encapsulation may also reduce or prevent host rejection in the case of xenogeneic (cross-species) or allogeneic transplantation.

Various types of cell devices are known. U.S. Pat. No. 4,892,538, to Aebischer et al. (incorporated herein by reference), discloses a selectively permeable hollow fiber membrane for cell encapsulation. U.S. Pat. No. 5,158,881, also to Aebischer et al. (incorporated herein by reference), discloses a method for encapsulating viable cells by forming a tubular extrudate around a cell suspension and sealing the tubular extrudate at intervals to define separate cell compartments joined by polymeric links. See also Mandel et al. (WO 91/00119), which refers to a selectively permeable cell closeable membrane tube for implantation in a subject having a large pore hydrophobic outer surface to encourage vascularization.

Many cell types used in encapsulated devices are of the adherent type, and (whether dividing or non-dividing) will aggregate and adhere to one another. These cell clusters or aggregations may form a necrotic core in the center of the device. Such a core may develop over time due to a shortage of certain metabolites reaching the center of the cell cluster or to the buildup of toxic products, causing cells to die. As dying cells accumulate and begin to break down, the necrotic tissue may also release factors which are detrimental to the surviving cells (e.g., factors which elicit a macrophage or other immune response).

One approach to reducing formation of a necrotic core involves immobilizing cells in a matrix material, e,g, a hydrogel matrix, within the device. See, e.g., Dionne et al. (WO 92/19195) which refers to biocompatible immunoisolatory vehicles with a hydrogel or extracellular matrix core.

Another known approach to controlling growth of cells in the device and to reducing necrotic core effects is to provide poly(hydroxyethyl methacylate) or poly(hydroxyethyl methacrylate-co-methyl methacrylate) or non-woven polyester scaffold for cells to grow on inside the device. See, e.g., Schinstine et al. (WO 96/02646). Such scaffolds form a fibrous net, not an open cell structure.

SUMMARY OF THE INVENTION

The present invention provides a new biocompatible cell device with an internal foam scaffold. The foam scaffold has an open cell structure, i.e., a structure presenting interconnected macropores. Cells can attach to the walls of the macropores. The scaffold material used in the devices of this invention is a synthetic, macroporous, polymeric, open-cell foam material. The cells contained on this scaffold material are prevented from escaping from the scaffold by encapsulation within a porous cell-impermeable membrane.

DETAILED DESCRIPTION OF THE INVENTION

This invention is directed to biocompatible devices with an internal foam scaffold. The devices of the present invention have at least one selectively permeable (permselective) surface across which biologically active molecules can be delivered. Delivery of such molecules can be from the device to the host or from the host to the device. The device may include means for introducing cells therein following implantation. See, e.g., Aebischer et al. (WO093/00128).

The devices of the instant invention comprise (a) a foam scaffold comprising a reticulated structure of interconnected pores, the pores being of a size that permits cell attachment to the pore walls, (b) living cells dispersed in or on said foam scaffold, and (c) a surrounding or peripheral region comprising a selectively permeable membrane jacket which is biocompatible. If desired, the device can be constructed to minimize the deleterious effects of the host's immune system on the cells in its core.

Prior art matrices used in hollow fiber membrane devices to immobilize cells have been crosslinked hydrogels. The foam scaffolds of this invention have several advantages over these traditional hydrogel matrices:

(1) Hydrogels in general do not inhibit cell growth and migration because they lack physical surfaces which constrain cells, whereas foams have interconnected pores with surfaces (or walls) onto which cells can attach. This can inhibit growth of contact-inhibited cells. Thus for proliferating contact-inhibited cell lines, foams can provide a stable cell number once the surface area has been filled with cells whereas in hydrogels cell proliferation remains uncontrolled.

(2) Foams can provide considerable mechanical strength, elasticity and added kink resistance to hollow fiber membranes whereas most hydrogels are mechanically weak and cannot provide kink resistance.

(3) Foams can be formed directly in the hollow fiber membranes and sterilized as part of the pre-assembled device eliminating the need to inject the matrix with cells in a separate aseptic step.

(4) Foams can keep cells distributed more evenly within the encapsulation device than with liquid core substrates employed as cell supports previously and can thus prevent cell clumping which leads to poor transport characteristics and possible subsequent necrotic cores within the lumen of the device.

(5) Synthetic foam materials are considerably more biologically stable than hydrogels that can be degraded by cells or enzymes.

(6) Synthetic non-degradable foams are non-fouling to the membrane—hydrogels may foul the pores of the permselective skin of the membrane upon loading into the device and as they degrade.

(7) Since foams physically separate small cell clusters from one another, they can support a higher cell density than hydrogel matrix materials if needed.

The foam scaffolds of this invention also have advantages over non-foam scaffolds. Foam scaffolds can be easily produced with defined characteristics and pore sizes. Further, prior art scaffolds typically have a fibrous net structure, rather than an open cell structure with interconnected pores, and thus have less surface available for cell attachment. Moreover, fibrous net scaffolds are generally more difficult to manufacture with reproducible physical characteristics, and generally cannot be prefabricated outside the membrane jacket. In addition, the reticulated macroporous structure of the foam scaffold permits fabrication of areas of cell permissiveness and cell non-permissiveness within the device, by filling the pores with a non-permissive material (e.g., a non-permissive hydrogel).

A "biocompatible device" means that the device, upon implantation in a host mammal, does not elicit a detrimental host response sufficient to result in the rejection of the device or to render the device inoperable. Such inoperability may occur, for example, by formation of a fibrotic structure around the device limiting diffusion of nutrients to the cells therein.

"Biological activity" refers to the biological effects of a molecule on a specific cell. As used herein, "a biologically active molecule" is a molecule which may exert its biological activity within the cell in which it is made (e.g., bcl-2 to prevent apoptosis) or it may be expressed on the cell surface and affect the cell's interactions with other cells or biologically active molecules (e.g., a neurotransmitter receptor or cell adhesion molecule). Additionally, a biologically active molecule may be released or secreted from the cell in which it is made and exert its effect on a separate target cell (e.g., a neurotransmitter, hormone, growth or trophic factor, or cytokine).

Various polymers and polymer blends can be used to manufacture the jacket of the encapsulation device. Polymeric membranes forming the device may include polyacrylates (including acrylic copolymers), polyvinylidenes, polyvinyl chloride copolymers, polyurethanes, polystyrenes, polyamides, cellulose acetates, cellulose nitrates, polysulfones (including polyethersulfones), polyphosphazenes, polyacrylonitriles, and PAN/PVC as well as derivatives, copolymer, and mixtures thereof.

Alternately, the device jacket may be formed from any suitable biocompatible material, including, e.g., hydrogels. See, e.g., Dionne et al. (WO 92/19195).

The device jacket may also include a hydrophobic matrix such as an ethylene vinyl acetate copolymer, or a hydrophilic matrix such as a hydrogel. The jacket may be post-production coated or treated with an impermeable outer coating such as a polyurethane, ethylene vinyl acetate, silicon, or alginate covering part of the cell chamber. The material used to form the jacket results in a surrounding or peripheral region which is selectively permeable and biocompatible.

The solvents used in conjunction with the above-identified polymers in forming the jacket will depend upon the particular polymer chosen for the membrane material. Suitable solvents include a wide variety of organic solvents such as alcohols and ketones generally as well as dimethylsulfoxide (DMSO), dimethylacetamide (DMA), and dimethylformamide (DMF) and blends of these solvents as well. In general, water-miscible organic solvents are preferred.

The polymeric solution (or "dope") can also include various additives such as surfactants to enhance the formation of porous channels and antioxidants to sequester oxides that are formed during the coagulation process. Exemplary surfactants include Triton-X 100 available from Sigma Chemical Corp. and Pluronics P65, P32, and P18. Exemplary anti-oxidants oxidants include vitamin C (ascorbic acid) and vitamin E.

The jacket allows passage of substances up to a predetermined size but prevents the passage of larger substances. More specifically, the jacket is produced in such a manner that it has pores or voids of a predetermined range of size. The molecular weight cutoff (MWCO) selected for a particular device will be determined in part by the application contemplated. Membranes most useful in the instant invention are ultrafiltration and microfiltration membranes.

In one embodiment, we contemplate ultrafiltration membranes. These are also known as selectively permeable or permselective membranes. In this embodiment, we contemplate a MWCO of 1000 kD or less, preferably between 50–700 kD or less, most preferably between 70–300 kD. In another embodiment, we contemplate microfiltration membranes, or microporous membranes, to form the jacket.

Any suitable membrane can be used to construct the devices with internal foam scaffolds of this invention. For example, hollow fiber permselective membranes as described in U.S. Pat. No. 4,892,538 (incorporated herein by reference) (e.g., XM-50 tubes from AMICON Corp., Lexington, Mass.) may be used. Alternately, selectively permeable hollow fiber membranes may be formed as described in U.S. Pat. Nos. 5,284,761 or 5,283,187, and Baetge et al. (WO 95/05452), all herein incorporated by reference. In one embodiment, the jacket is formed from a polyethersulfone membrane of the types described in U.S. Pat. Nos. 4,976,859 and 4,968,733, (referring to permselective and microporous membranes), which disclosures are incorporated herein by reference.

Various methods for forming permeable membranes are known in the art. In one method, hollow fiber membranes are formed by coextrusion of a polymeric casting solution and a coagulant (which can include biological tissue fragments, organelles, or suspensions of cells and/or other therapeutic agents). Such a method is referred to in U.S. Pat. Nos. 5,284,761 and 5,283,187, incorporated herein by reference.

Preferably, the devices of this invention are immunoisolatory. An "immunoisolatory device" means that the device upon implantation into a mammalian host minimizes the deleterious effects of the host's immune system on the cells within its core such that the device functions for extended periods of time in vivo. To be immunoisolatory, the surrounding or peripheral region of the device should confer protection of the cells from the immune system of the host in whom the device is implanted, by preventing harmful substances of the host's body from entering the core of the vehicle, and by providing a physical barrier sufficient to prevent detrimental immunological contact between the encapsulated (isolated) cells and the host's immune system. The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thickness of 20 to 75 microns are particularly preferred. Types of immunological attack which can be prevented or minimized by the use of the instant vehicle include attack by macrophages, neutrophils, cellular immune responses (e.g., natural killer cells and antibody-dependent T cell-mediated cytolysis (ADCC), and humoral response (e.g., antibody-dependent, complement-mediated cytolysis).

Use of immunoisolatory devices allows the implantation of xenogeneic cells or tissue, without a concomitant need to immunosuppress the recipient. The exclusion of IgG from the core of the vehicle is not the touchstone of immunoisolation, because in most cases IgG alone is insufficient to produce cytolysis of the target cells or tissues. Using immunoisolatory devices, it is possible to deliver needed high molecular weight products or to provide metabolic functions pertaining to high molecular weight substances, provided that critical substances necessary to the mediation of immunological attack are excluded from the immunoisolatory device. These substances may comprise the complement attack complex component Clq, or they may comprise phagocytic or cytotoxic cells; the instant immunoisolatory device provides a protective barrier between these harmful substances and the isolated cells.

The foam scaffold may be formed from any suitable material that forms a biocompatible foam with an open cell or macroporous structure with a network of pores. An open-cell foam is a reticulate structure of interconnected pores. The foam scaffold provides a non-biodegradable, stable scaffold material that allows attachment of adherent cells. Among the polymers that are useful in forming the foam scaffolds for the devices of this invention are thermoplastics and thermoplastic elastomers.

Some examples of materials useful in forming suitable foam scaffolds are listed in Table 1.

TABLE 1

| Thermoplastics: | Thermoplastic Elastomers: |
| --- | --- |
| Acrylic | Polyamide |
| Modacrylic | Polyester |
| Polyamide | Polyethylene |
| Polycarbonate | Polypropylene |
| Polyester | Polystyrene |

TABLE 1-continued

| Thermoplastics: | Thermoplastic Elastomers: |
| --- | --- |
| Polyethylene | Polyurethane |
| Polypropylene | Polyvinyl Alcohol |
| Polystyrene | Silicone |
| Polysulfone | |
| Polyethersulfone | |
| Polyvinylidene fluoride | |

Thermoplastic foam scaffolds made from polysulfone and polyethersulfone, and thermoplastic elastomer foam scaffolds made from polyurethane and polyvinyl alcohol, are preferred.

The foam must have some (but not necessarily all) pores of a size that permits cells to attach to the walls or surfaces within the pores. The pore size, pore density and void volume of the foam scaffold may vary. The pore shape may be circular, elliptical or irregular. Because the pore shape can vary considerably, its dimensions may vary according to the axis being measured. For the purposes of this invention, at least some pores in the foam should have a pore diameter of between 20–500 $\mu$m, preferably between 50–150 $\mu$m. Preferably the foregoing dimensions represent the mean pore size of the foam. If non-circular, the pore may have variable dimensions, so long as its size is sufficient to permit adherent cells to attach to the walls or surfaces within the pore. In one embodiment, foams are contemplated having some elliptical pores that have a diameter of 20–500 $\mu$m along the minor axis and a diameter of up to 1500 $\mu$m along the major axis.

In addition to the foregoing cell permissive pores sizes, preferably a least a fraction of the pores in the foam should be less than 10 $\mu$m to be cell impermissive but still provide channels for transport of nutrients and biologically active molecules throughout the foam.

Pore density of the foam (i.e., the number per volume of pores that can accommodate cells, as described above) can vary between 20–90%, preferably between 50–70%.

Similarly, the void volume of the foam may vary between 20–90%, preferably between 30–70%.

The walls or surfaces of the pores are typically coated with an extracellular matrix molecule or molecules, or other suitable molecule. This coating can be used to facilitate adherence of the cells to the walls of the pores, to hold cells in a particular phenotype and/or to induce cellular differentiation.

Preferred examples of extracellular matrix molecules (ECM) that can be adhered to the surfaces within the pores of the foams include: collagen, laminin, vitronectin, polyornithine and fibronectin. Other suitable ECM molecules include glycosaminoglycans and proteoglycans; such as chrondroitin sulfate, heparin sulfate, hyaluron, dermatan sulfate, keratin sulfate, heparan sulfate proteoglycan (HSPG) and elastin.

The ECM may be obtained by culturing cells known to deposit ECM, including cells of mesenchymal or astrocyte origin. Schwann cells can be induced to synthesize ECM when treated with ascorbate and cAMP. See, e.g., Baron-Van Evercooren et al., "Schwann Cell Differentiation in vitro: Extracellular Matrix Deposition and Interaction," *Dev. Neurosci.*, 8, pp. 182–96 (1986).

In addition, adhesion peptide fragments, e.g., RGD containing sequences (ArgGlyAsp), YIGSR-containing sequences (TyrIleGlySerArg), as well as IKVAV containing sequences (IleLysValAlaVal), have been found to be useful in promoting cellular attachment. Some RGD-containing molecules are commercially available—e.g., PepTite-2000™ (Telios).

The foam scaffolds of this invention may also be treated with other materials that enhance cellular distribution within the device. For example, the pores of the foam may be filled with a non-permissive hydrogel that inhibits cell proliferation or migration. Such modification can improve attachment of adherent cells to the foam scaffold. Suitable hydrogels include anionic hydrogels (e.g., alginate or carageenan) that may repel cells due to charge. Alternately, "solid" hydrogels (e.g., agarose or polyethylene oxide) may also be used to inhibit cell proliferation by discouraging binding of extracellular matrix molecues secreted by the cells.

Treatment of the foam scaffold with regions of a non-permissive material allows encapsulation of two or more distinct cell populations within the device without having one population overgrow the other. Thus non-permissive materials may be used within the foam scaffold to segregate separate populations of encapsulated cells. The distinct populations of cells may be the same or different cell types, and may produce the same or different biologically active molecules. In one embodiment, one cell population produces a substance that augments the growth of the other cell population. In another embodiment, multiple cell types producing multiple biologically active molecules are encapsulated. This provides the recipient with a mixture or "cocktail" of therapeutic substances.

It will be appreciated that the devices of the present invention may have a variety of shapes. The device can be any configuration appropriate for maintaining biological activity and providing access for delivery of the product or function, including for example, cylindrical, rectangular, disk-shaped, patch-shaped, ovoid, stellate, or spherical. Moreover, the device can be coiled or wrapped into a mesh-like or nested structure. If the device is to be retrieved after it is implanted, configurations which tend to lead to migration of the devices from the site of implantation, such as spherical devices small enough to migrate in the patient, are not preferred. Certain shapes, such as rectangles, patches, disks, cylinders, and flat sheets offer greater structural integrity and are preferable where retrieval is desired.

The foam scaffold is adapted to fit the device, as appropriate. For tubular (or "hollow fiber") embodiments, the foam scaffold may form a cylindrical tube or rod, a rectangular tube or rod, or any other oblique shape, so long as it can fit within the lumen of the hollow fiber. It will be appreciated that in some embodiments, the foam scaffold may have fins or other protrusions which may contact the inner wall of the hollow fiber.

In one embodiment of the invention, the cell device is formed from a hollow fiber membrane with a cylindrical internal foam scaffold.

The device may also be in the form of a flat sheet device. Flat sheet devices are described in detail in Dionne et al. (WO 92/19195). A flat sheet device of this invention is generally characterized by a first flat sheet membrane with a first interior surface, and a second flat sheet membrane with a second interior surface, the two membranes sealed at their periphery to provide an enclosure, with the foam scaffold positioned between the membranes, inside the enclosure. Cells may then be introduced through an access port, and the seal completed with a plug inserted into the port.

The devices of this invention may be formed according to any suitable method. In one embodiment, the foam scaffold may be pre-formed and inserted into a pre-fabricated jacket, e.g., a hollow fiber membrane, as a discrete component.

Any suitable thermoplastic or thermoplastic elastomer foam scaffold material may be preformed for insertion into a pre-fabricated jacket. In one embodiment we prefer polyvinyl alcohol (PVA) sponges for use as the foam scaffold. Several PVA sponges are commercially available. For example, PVA foam sponges #D-3, 60 $\mu$m pore size are suitable (Rippey Corp, Kanebo). Similarly, PVA sponges are commercially available from Unipoint Industries, Inc. (Thomasville, N.C.) and Ivalon Inc. (San Diego, Cailf.). PVA sponges are water-insoluble foams formed by the reaction of aerated Poly(vinyl alcohol) solution with formaldehyde vapor as the crosslinker. The hydroxyl groups on the PVA covalently crosslink with the aldehyde groups to form the polymer network. The foams are flexible and elastic when wetted and semi-rigid when dried.

In an alternate embodiment, the foam scaffold may be formed in situ within a pre-fabricated jacket. Any suitable thermoplastic or thermoplastic elastomer foam precursor may be used to form a foam scaffold in situ. Polyvinyl alcohol, polyurethane, polysulfone, and polyether sulfone are preferred for forming the scaffold in situ.

In one preferred embodiment, the foam scaffold can be formed in situ using polyurethanes. Polyurethanes are polymers formed by reaction of polyisocyanates with polyhydroxy compounds. Polyurethane foam matrix materials may be formed within the hollow fiber membrane using prepolymers (formed through the reaction of a linear OH-terminated polymer with an excess of diisocyanate resulting in an isocyanate-terminated polymer) which polymerize upon contact with aqueous solutions and generate $CO_2$ as a product of the polymerization. The $CO_2$ gas produced forms the open-cell foam structures of the matrix materials. See, e.g., Hasirci, "Polyurethanes" in *High Performance Biomaterials: A Comprehensive Guide to Medical and Pharmaceutical Applications* (Szycher, ed.) (Technomic Publishing, Lancaster, Pa. 1991), pp. 71–89.

A surfactant may be added to the aqueous solution to facilitate pore formation in the foam. Exemplary surfactants include Triton-X 100 available from Sigma Chemical Corp. and Pluronics P65, P32, and P18. Polyurethane foam precursor materials, and a suitable surfactant for forming foams suitable in this invention are available commercially from Hampshire Chemical Corp. (Lexington, Mass.).

In a further embodiment, the foam scaffold may be pre-formed and then coated with a cell impermeable jacket. Again, any suitable thermoplastic or thermoplastic elastomer foam precursor may be used to form the foam scaffold in situ. Formation of the jacket around the scaffold can be achieved according to the methods such as those detailed in Dionne et al. (WO 92/19195).

In one preferred embodiment, polyethylene foam rods formed by sintering beads of high density polyethylene (HDPE) (Porex®) having average pore sizes ranging form 30–60 $\mu$m can be composited with a permselective PAN/PVC membrane by a dipcoating procedure. Other sintered thermoplastic material is commercially available from, e.g., Interflo Technologies (Brooklyn, N.Y.). The foam rods are dipcoated with PAN/PVC dissolved in DMSO solvent, and phase inverted to form the membrane by immersion in a non-solvent water bath. The foam rods can also be coated with poly-ornithine to improve cell adhesion to the foam material prior to infusing devices with cells.

Preferably the device has a tether that aids in retrieval. Such tethers are well known in the art.

The devices of this invention have a core of a preferable minimum volume of about 1 to 10 μl and depending upon use are easily fabricated to have a volume in excess of 100 μl (the volume is measured in the absence of the foam scaffold).

In a hollow fiber configuration, the fiber preferably has an inside diameter of less than 1500 microns, more preferably approximately 300–600 microns. If a semi-permeable membrane is used, the hydraulic permeability is preferably in the range of 1–100 mls/min/M²/mmHg, more preferably in the range of 25 to 70 mls/min/M²/mmHg. The glucose mass transfer coefficient of the device, defined, measured and calculated as described by Dionne et al., *ASAJO Abstracts*, p. 99 (1993), and Colton et al., *The Kidney* (Brenner and Rector, eds.) (1981), pp. 2425–89 is preferably greater than $10^{-6}$ cm/sec, more preferably greater than $10^{-4}$ cm/sec.

Any suitable method of sealing the devices may be used, including the employment of polymer adhesives and/or crimping, knotting and heat sealing. These sealing techniques are known in the art. In addition, any suitable "dry" sealing method can also be used. In such methods, a substantially non-porous fitting member is provided which is attached to the membrane encapsulation device with a secure dry seal and the cell-containing solution is introduced through such fitting member. Subsequent to filling, the device is sealed by closing the opening in the non-porous fitting. Such a method is described in Mills et al. (WO 94/01203), incorporated herein by reference.

A wide variety of cells may be used in this invention. These include well known, publicly available immortalized cell lines (including conditionally immortalized cells) as well as dividing primary cell cultures. Examples of publicly available cell lines suitable for the practice of this invention include baby hamster kidney (BHK), Chinese hamster ovary (CHO), mouse fibroblast (L-M), NIH Swiss mouse embryo (NIH/3T3), African green monkey cell lines (including COS-a, COS-7, BSC-1, BSC40, BMT-10 and Vero), rat adrenal phcochromocytoma (PC12 and PC12A), rat glial tumor (C6), RIN cells, β-TC cells, Hep-G2 cells, and myoblast cell lines (including C2C12 cells)

Primary cells that may be used according to the present invention include neural progenitor-stem cells derived from the CNS of mammals (see, Richards et al., *Proc. Natl. Acad. Sci. USA*, 89: 8591–95 (1992); Ray et al., *PNAS*, 90: 3602–06 (1993)), primary fibroblasts, Schwan cells, astrocytes, oligodendrocytes and their precursors, myoblasts, adrenal chromaffin cells, and the like.

The choice of cell depends upon the intended application. The cells may naturally produce the desired biologically active molecule or may be genetically engineered to do so.

A gene of interest (i.e., a gene that encodes a suitable biologically active molecule) can be inserted into a cloning site of a suitable expression vector by using standard recombinant DNA techniques. It will be appreciated that more than one gene may be inserted into a suitable expression vector. These techniques are well known to those skilled in the art.

The expression vector containing the gene of interest may then be used to transfect the desired cell line. Standard transfection techniques such as calcium phosphate co-precipitation, DEAE-dextran transfection or electroporation may be utilized. Commercially available mammalian transfection kits may be purchased from e.g., Stratagene (La Jolla, Calif.).

A wide variety of host/expression vector combinations may be used to express the gene encoding the biologically active molecule. Suitable promoters include, for example, the early and late promoters of SV40 or adenovirus and other known non-retroviral promoters capable of controlling gene expression. Useful expression vectors, for example, may consist of segments of chromosomal, non-chromosomal and synthetic DNA sequences, such as various known derivatives of SV40 and known bacterial plasmids, e.g., pUC, pBlueScript™, pBR322, pCR1, pMB9, pUC, pBlueScript™ and their derivatives. Expression vectors containing the geneticin (G418) or hygromycin drug selection genes (see, e.g., Southern, P. J., *In Vitro*, 18: 315 (1981) and Southern, P. J. and Berg, P., *J. MolAppl. Genet.*, 1: 327 (1982)) are also useful. Expression vectors containing the zeocin drug selection gene are also contemplated. Examples of commercially available expression vectors that can be employed are pRC/CMV, pRC/RSV, and PCDNA1NEO (In Vitrogen). The viral promoter regions of such vectors directing the transcription of the drug selection and biologic genes of interest are advantageously replaced with one of the above promoter sequences that are not subject to the down regulation experienced by viral promoters within the CNS. For example, the GFAP promoter would be employed for the transfection of astrocytes and astrocyte cell lines, the TH promoter would be used in PC12 cells, or the MBP promoter would be used in oligodendrocytes.

In one embodiment, the pNUT expression vector is used. See, Baetge et al., *PNAS*, 83: 5454–58 (1986). In addition, the pNUT expression vector can be modified such that the DHFR coding sequence is replaced by the coding sequence for G418 or hygromycin drug resistance. The SV40 promoter within the pNUT expression vector can also be replaced with any suitable constitutively expressed mammalian promoter, such as those discussed above. The pNUT vector contains the cDNA of the mutant DHFR and the entire pUC18 sequence including the polylinker (Baetge et al., supra). The DHFR transcription unit is driven by the SV40 promoter and fused at its 3' end with the hepatitis B virus gene polyadenylation signal (approximately 200 bp 3' untranslated region) to ensure efficient polyadenylation and maturation signals.

Any suitable biologically active molecule can be produced by the encapsulated cells. The biologically active molecules contemplated include neurotransmitters. Typically these are small molecules (less than 1,000 Daltons molecular weight) which act as chemical means of communication between neurons. Such neurotransmitters include dopamine, gamma aminobutyric acid (GABA), serotonin, acetylcholine, noradrenaline, epinephrine, glutamic acid, and other peptide neurotransmitters. Likewise, we contemplate production of agonists, analogs, derivatives or fragments of neurotransmitters which are active, including, for example, bromocriptine (a dopamine agonist) and L-dopa (a dopamine precursor).

Other biologically active molecules contemplated include hormones, cytokines, growth factors, trophic factors, angiogenesis factors, antibodies, blood coagulation factors, lymphokines, enzymes, analgesics and other therapeutic agents or agonists, precursors, active analogs, or active fragments thereof. These include enkephalins, catecholamines (e.g., norepinephrine and epinephrine), endorphins, dynorphin, insulin, factor VIII, erythropoietin, Substance P, nerve growth factor (NGF), Glial-derived Neurotrophic Factor (GDNF), platelet-derived growth factor (PDGF), epidermal growth factor (EGF), brain-derived neurotrophic factor (BDNF), neurotrophin-3 (NT-3), neurotrophin-4/5 (NT4/5), an array of fibroblast growth factors, and ciliary neurotrophic factor (CFNT).

Alternatively, the encapsulated cells may produce a biologically active molecule that acts on substances that are delivered into the device. For example, the device may contain one or more cells or substances which "scavenge" cholesterol, or other undesireable molecules from the host. In such instances, the device provides a biological function to the patient.

In some aspects of the invention, the cell is allogeneic (i.e.. from another of the same species as the subject in which it is to be implanted), autologous or syngeneic (i.e., from the same individual), or xenogeneic (i.e., from another of a different species).

The devices are designed for implantation into a recipient. The recipient may be any suitable animal, preferably a mammal, most preferably a human patient. Any suitable surgical implantation technique may be used. A preferred system for implanting capsular devices is described in U.S. Pat. No. 5,487,739, incorporated herein by reference.

Any suitable implantation site may be utilized. In one embodiment, treatment of diabetes by delivery of insulin is contemplated. In this embodiment, implantation into the peritoneal cavity is preferred.

In another embodiment, implantation into the central nervous system (CNS) is contemplated. The devices of this invention may be used in the treatment or prophylaxis of a wide variety of neurological diseases, disorders or conditions. These include Huntingtons, Parkinsons, amyotropic lateral sclerosis, and pain, as well as cancers or tumors. Suitable sites in the CNS include the brain ventricles, the parenchyma, the cerebrospinal fluid (CSF), the striatum, the cerebral cortex, subthalamic nuclei, and nucleus Basalis of Maynert. One preferred CNS site is the CSF, most preferably the subarachnoid space.

The dosage of the biologically active molecule can be varied by any suitable method known in the art. This includes changing the cellular production of the biologically active molecule, achieved in any conventional manner, such as varying the copy number of the gene encoding the biologically active molecule in the transduced cell, or driving expression of the biologically active molecule using a higher or lower efficiency promoter, as desired. Further, the device volume and cell loading density can easily be varied, over at least three orders of magnitude. Preferred loadings range between $10^{3-107}$ cells per device. In addition. dosage may be controlled by implanting a fewer or greater number of devices. Preferably, one to ten devices per patient will be implanted.

In order that this invention may be better understood, the following examples are set forth. These examples are for purposes of illustration only and are not to be construed as limiting the scope of this invention in any manner.

EXAMPLES

Example 1
PC12 Cells Encapsulated within Hollow Fiber Membranes with a Polyvinylalcohol (PVA) Foam Scaffold
Foam and Hollow Fiber Preparation Procedure Permselective hollow fibers were prepared using the wet-dry spinning technique of Cabasso, *Encyclopedia of Chemical Technology,* 12:492–517 (1980). The asymmetric hollow fibers were cast from 12.5% polyacrylonitrile polyvinyl chloride (PAN/PVC) copolymer in dimethyl sulfoxide (w/w) (DMSO) solvent. Single-skinned fibers were produced using this method. The hollow fibers were spun into a non-solvent water bath, soaked in 25% glycerin overnight then dried. In this set of experiments, the hollow fiber membranes used were single-skinned PAN/PVC copolymer with inner diameter of 680 $\mu$m and wall thickness of 85 $\mu$m.

Several commercially available PVA sponges were used to form the foam scaffold in the devices of this invention. These included PVA foam sponges from the following manufacturers:

(1) #D-3 PVA from Rippey Corp. (Kanebo). This foam has a 60 $\mu$m mean pore size, an apparent specific gravity of 0.094 g/cm$^3$, tensile strength at breakage of 5.9 kg/cm$^2$, and softens with water content, swelling slightly. See, e.g., "PVA Sponge Material Technical Manual", Rippey Corp.

(2) PVA foam from Unipoint Industries, Inc. (Thomasville, N.C.) having characteristics substantially similar to the Rippey foam. This foam is described in U.S. Pat. No. 2,609,347, incorporated herein by reference.

(3) PVA foam from Ivalon Inc. (San Diego, Calif.) having characteristics substantially similar to the Rippey foam.

For encapsulation in hollow fiber membranes (HFM), we cut the foams with a microtome into rectangular "matchsticks" or alternatively bored them with steel microborers into cylinders. These foam cylinders are bored to have diameters (when dry) of approximately 50–100 microns less than that of the hollow fiber membranes used. The length was approximately 1 cm.

The PVA foam cylinders were then coated with Type IV collagen derived from human placenta (Sigma Chemical, #C5533) by soaking overnight in a 1 mg/mL collagen solution prepared in PBS buffer. The foams were then removed from the collagen solution and allowed to dry completely under a UV lamp in a laminar flow hood.

The foam cylinders were then inserted into hollow fiber membranes prior to sterilization and cell loading. A septal hub assembly with an access for cell loading was attached to the foam/HFM composite. Such a hub assembly is described, e.g., in Mills et al. (WO 94/01203). The foam/HFM composite device was sterilized by ethanol soaking or alternatively by ethylene oxide (ETO) gas sterilization.

PVA foams expand by approximately 20% in volume upon wetting. Thus, cell media was first injected into the lumen of the fiber to sufficiently wet the foam to fill the lumen and eliminate the gap between the foam and the membrane, prior to cell loading.

We used PC12 cells in this experiment. PC12 adherent cells were scraped to remove them from culture flasks. The cells were resuspended in medium and pelleted by centrifugation at 1000 rpm for 2 minutes. The cells were then resuspended in medium to a final concentration of 50,000 cells/$\mu$L.

We compared devices having internal foam scaffolds of this invention with prior art devices having a hydrogel matrix core. Cells were loaded into 1 cm long hollow fiber devices using a glass Hamilton syringe. For foam scaffold devices, we loaded 2 $\mu$L of cells suspended in media. For prior art hydrogel matrix core devices, we loaded 2 $\mu$L of a cell/chitosan slurry (2% chitosan solution prior to 1:2 dilution with cell suspension).

After cell loading, the septum of the loading hub was cracked off and the access port sealed with a light-cured acrylate (Luxtrak LCM 24, ICI Resins US, Wilmington, Mass.).

The following hollow fiber encapsulated devices were prepared in the above manner:

(1) chitosan matrix with cell density of 50,000 cells/$\mu$L (2) PVA foam matrix with cell density of 100,000 cells/$\mu$L Devices were held in vitro for 6 weeks. The encapsulated cell loaded devices were maintained in a 37° C. humidified incubator and cell medium replenished 3 times/week.

Figure 1:
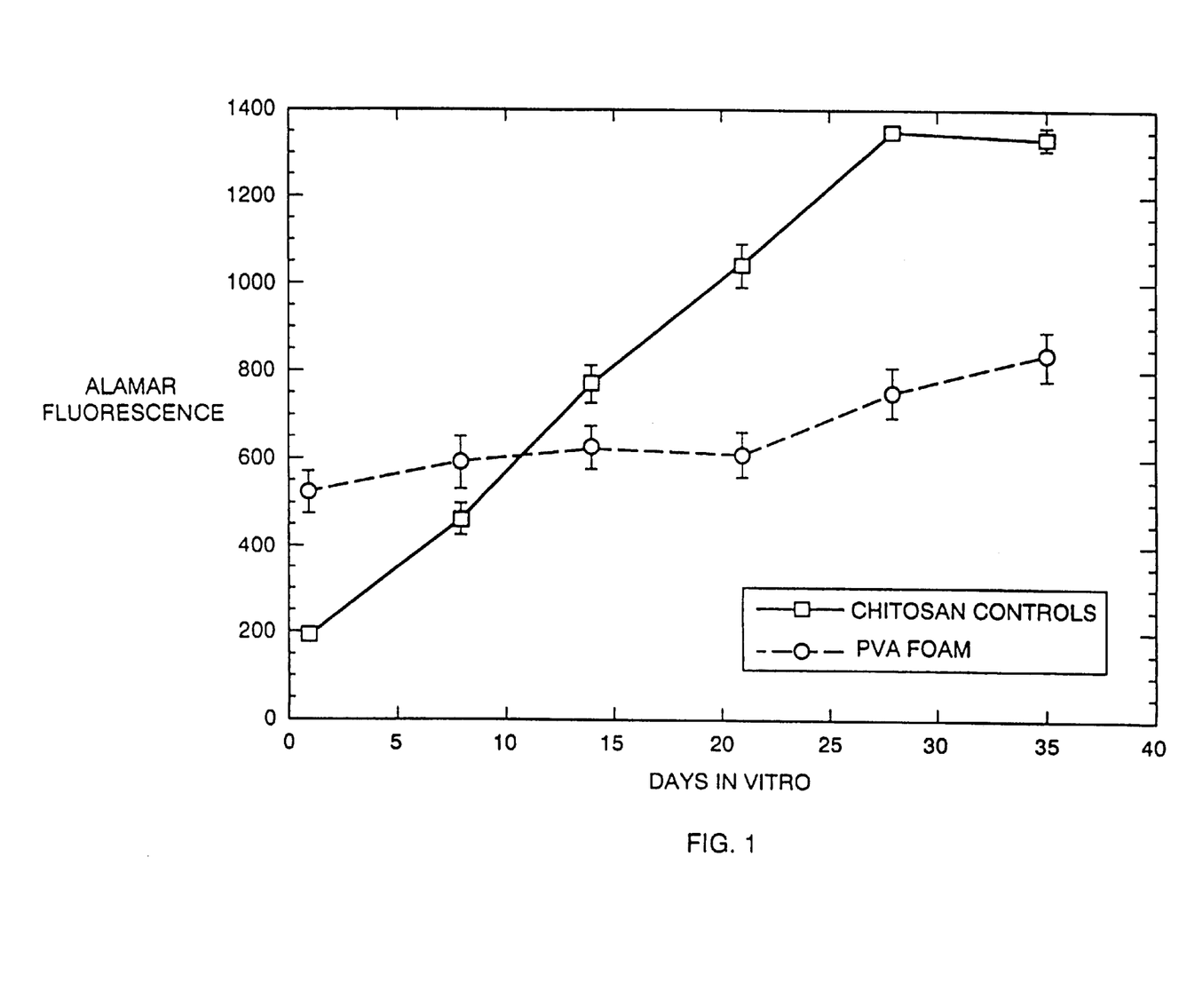
FIG. 1 is a graph of Alamar fluorescence from PC12 cells over time in a comparison of devices with a PVA foam scaffold (closed circles) and devices with a chitosan matrix (open squares).

Cell growth rate was monitored weekly with Alamar Blue® assay. The Alamar Blue assay is a quantitative measurement of the proliferation of human and animal cell lines which incorporates a fluorometric/colorimetric growth indicator based on detection of metabolic activity. The Alamar data (FIG. 1) indicate that the cell proliferation in devices with PVA foam matrix slowed dramatically over the course of the experiment compared to the approximate linear increase with time observed in the chitosan matrix devices. At the end point of the experiment, based on the Alamar data, the cell number in prior devices was almost two-fold that of the foam scaffold devices of this invention.

Figure 2:
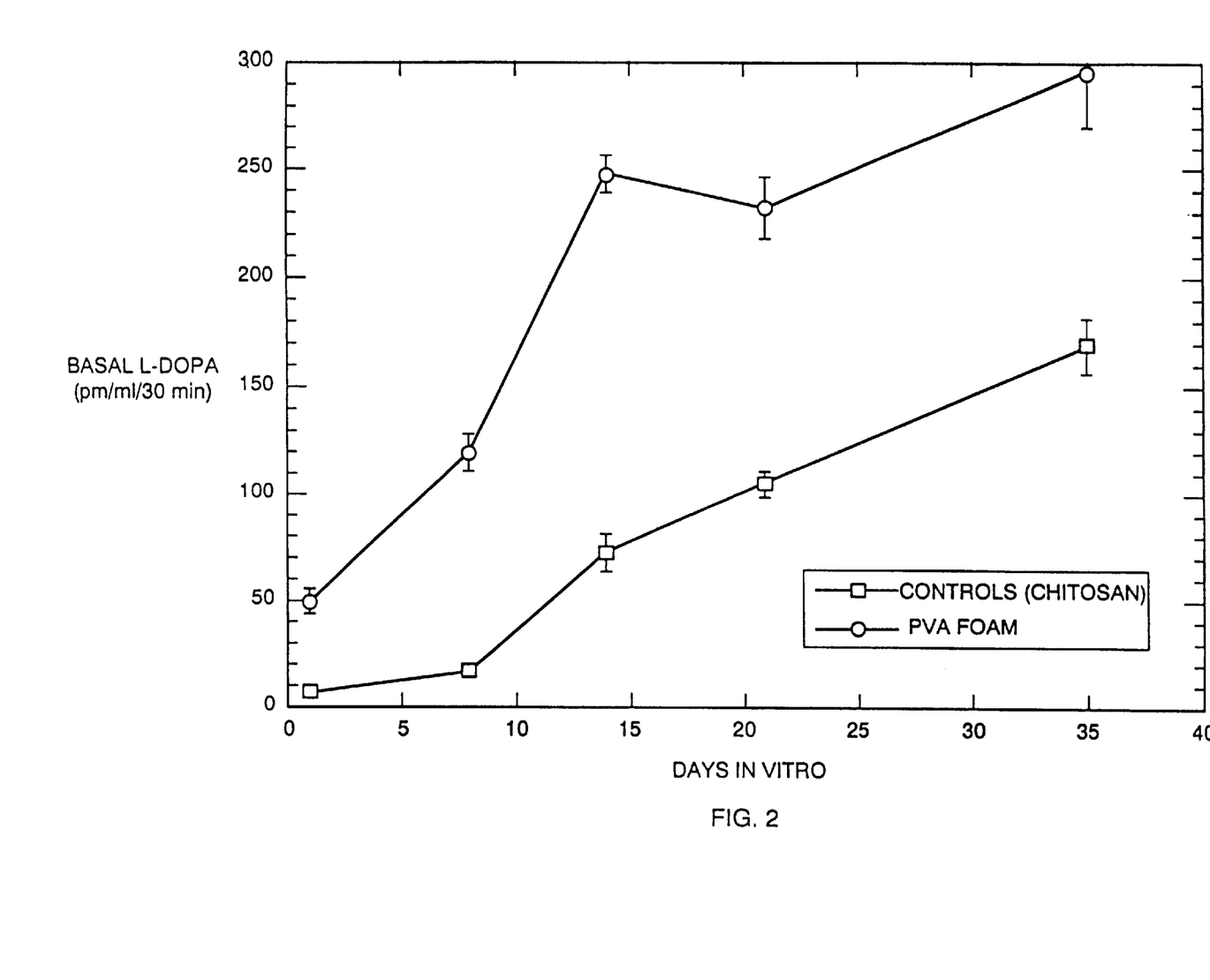
FIG. 2 is a graph of basal L-dopa release (pm/mL/30 min) from PC12 cells over time in a comparison of devices with a PVA foam scaffold (closed circles) and devices with a chitosan matrix (open squares).

The encapsulated cells were tested for basal and potassium-evoked catecholamines release weekly. As FIG. 2 shows, the basal L-dopa release indicates that the cells in the foam scaffold devices produced more catecholamines than cells encapsulated in the chitosan matrix devices, particularly at the end point of the experiment.

Representative devices were fixed and sectioned and stained with Hematoxylin and eosin at 2 weeks; all remaining devices were fixed and stained at 6 weeks. Histology sections showed that the PC12 cells encapsulated with a PVA foam matrix have a predominantly flattened differentiated morphology. In contrast, PC12 cells in the chitosan matrix devices had a more rounded morphology.

Large clusters of cells were seen in the chitosan matrix devices after 2 weeks in vitro. In contrast, cells in PVA matrix devices were primarily flattened in monolayers within the pores of the foam and had excellent distribution throughout the hollow fiber membrane.

After 6 weeks in vitro, the chitosan matrix devices showed large necrotic cores. In contrast, the PVA foam devices after 5 weeks showed some small necrotic areas; however, these areas of necrosis in the foam devices were not concentrated at the center of the device but randomly dispersed in the device.

Example 2
PC12 Cells Encapsulated within Hollow Fiber Membranes with PVA Foam Matrix Implanted Into a Rodent Host In addition to the in vitro example above, devices also were implanted into rodent hosts (Sprague-Dawley rats) to evaluate the in vivo performance of the foam scaffold devices compared with the prior art matrix core devices.

Figure 3:
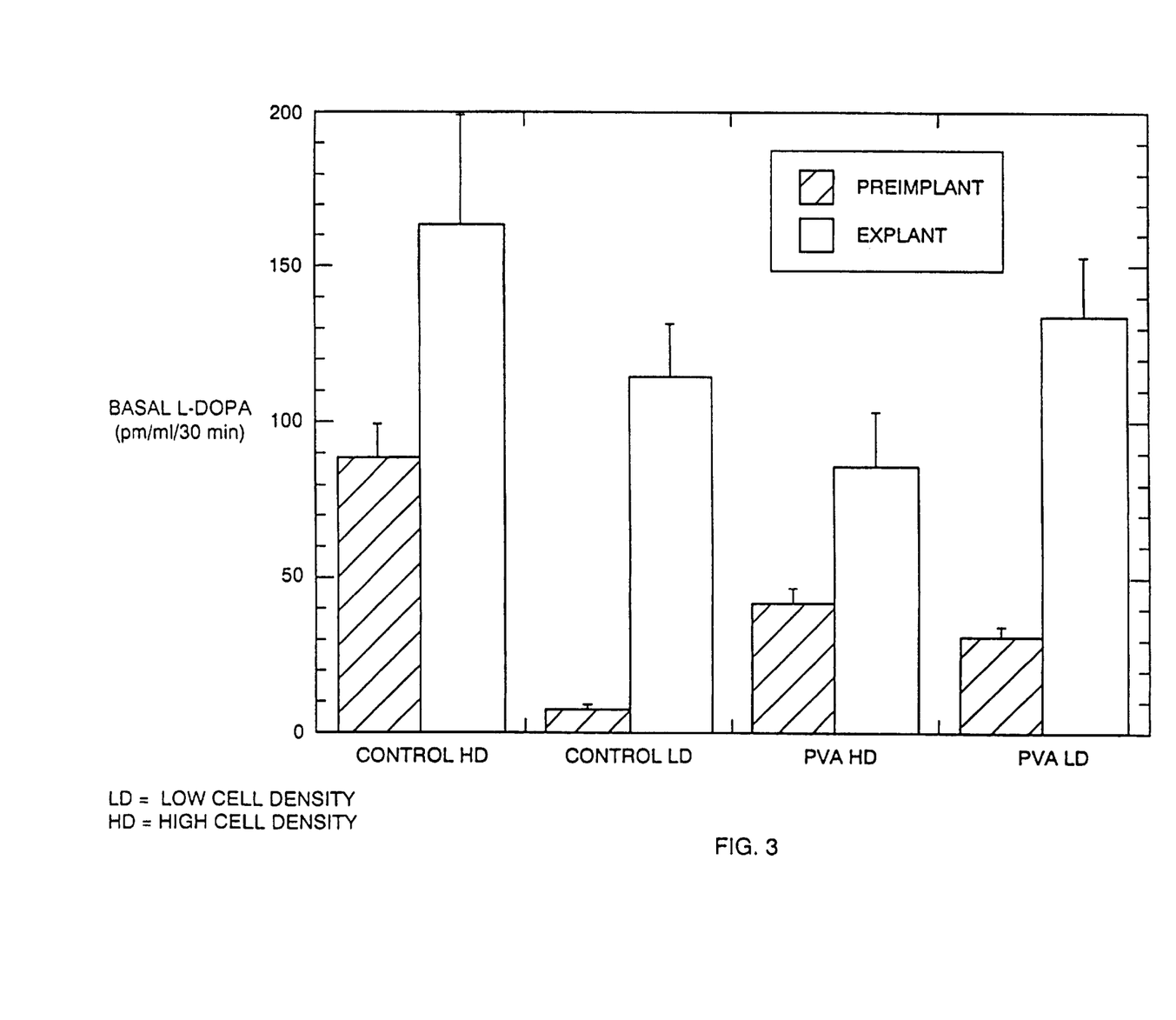
FIG. 3 is a graph of basal L-dopa release from PC12 cells before implant and at explant after a 1 month implant in rodents. The graph shows a comparison of devices with a PVA foam scaffold (labelled as PVA) and devices with a chitosan matrix (labelled as control). The hatched bars represent pre-implant data; the solid bars represent explant data. The devices were initially loaded with a low density (LD) of cells, or a high density (HD) of cells.
Figure 4:
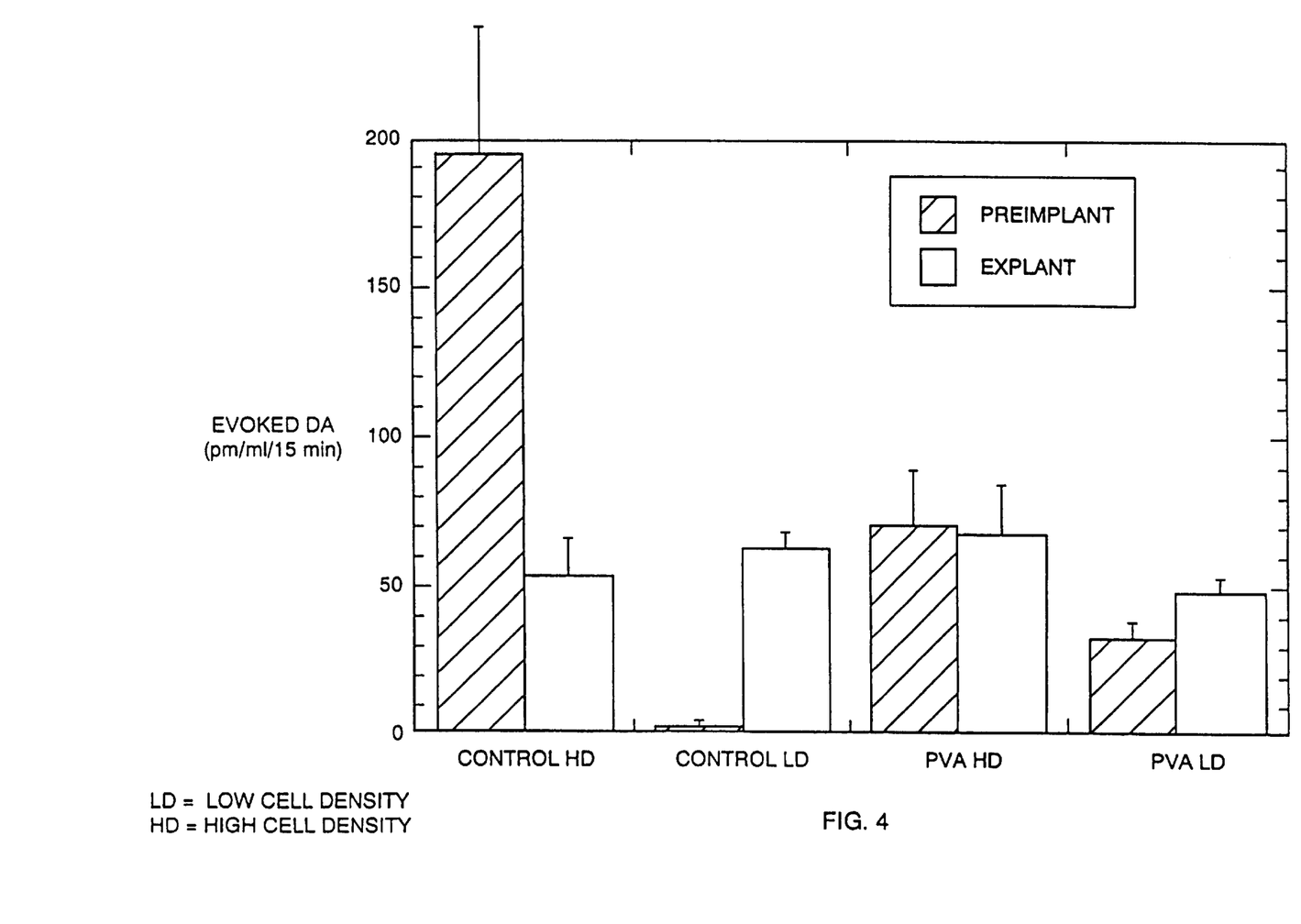
FIG. 4 is a graph of K-evoked L-dopa release from PC12 cells before implant and at explant after a 1 month implant in rodents. The graph shows a comparison of devices with a PVA foam scaffold (labelled as PVA) and devices with a chitosan matrix (labelled as control). The hatched bars represent pre-implant data; the solid bars represent explant data. The devices were initially loaded with a low density (LD) of cells, or a high density (HD) of cells.

The devices were implanted in the striatum in the brain. Devices were implanted bilaterally, with each host receiving one PVA foam device and one chitosan matrix device, both loaded with PC12 cells. Devices were manufactured as in Example 1, except with the following cell loading densities:

(1) precipitated chitosan matrix with cell density of 50,000 cells/$\mu$L
(2) PVA foam matrix with cell density of 50,000 cells/$\mu$L
(3) precipitated chitosan matrix with cell density of 100,000 cells/$\mu$L
(4) PVA foam matrix with cell density of 100,000 cells/$\mu$L The encapsulated cells were tested for basal- and potassium-evoked catecholamine release one week after encapsulation (pre-implant) and immediately post-explant. The results are shown in FIGS. 3 and 4.

Cell number (as indicated by K+evoked dopamine release) appeared to remain relatively constant in the PVA foam devices for both high density (100,000 cells/$\mu$L) and low density (50,000 cells/$\mu$L) initial cell loadings. In contrast, K+dopamine secretion in the prior art chitosan matrix devices decreased dramatically for the high density devices. See FIG. 4. One explanation for this may be that these devices had grown to the upper limit of cell number they can support within the 1-week holding period prior to implantation. The K+dopamine secretion data also suggests that the low density seeded chitosan devices were still increasing in cell number when explanted.

These in vivo results are consistent with the in vitro discoveries reported in Example 1.

Example 3
BHK-hCNTF Cells Encapsulated within Hollow Fiber Membranes with PVA Foam Matrix and Cell-impermissive Hydrogel In this experiment baby hamster kidney (BHK) cells transfected to secrete human ciliary neurotrophic factor (hCNTF) were encapsulated. A pNUT-hCNTF-TX construct was incorporated into BHK cells using a standard calcium phosphate-mediated transfection method, as described in Baetge et al. (WO 95/05452). The cells were grown in DMEM with 10% fetal bovine serum and 2 mM L-glutamine, harvested with trypsin and resuspended as a single-cell suspension in PCI media for encapsulation. The cells were encapsulated in PVA foam matrix-containing devices as described in Example 1.

After loading PVA foam devices (constructed as described in Example 1) with 2 $\mu$L cell suspension in medium, the pores of the foams were filled with 2% sodium alginate prepared in calcium- and magnesium-free HBSS solution, then cross-linked with 1% calcium chloride for 5 minutes. The alginate gel provides a cell-impermissive region while the cells remain flattened against the walls of the foam within the device, preventing the cells from agglomerating.

Example 4
Mouse $C_2C_{12}$ Myoblast Cells Encapsulated within Hollow Fiber membranes with PVA Foam Matrix In this example, $C_2C_{12}$ myoblast cells were encapsulated in foam scaffold-containing devices prepared as described in Example 1. The $C_2C_{12}$ myoblast cells were grown in DMEM medium with 10% fetal bovine serum. The cells were loaded into hollow fiber membrane devices as in Example 1, in PC1 medium. Differentiation of myoblasts into the post-mitotic state after encapsulation occurred by the elimination of serum from the holding medium.

Example 5
Neural Stem Cells Encapsulated within Hollow Fiber Membranes with Polyethylene Foam Matrix Polyethylene foam rods formed by sintering beads of high density polyethylene (HDPE) (Porex®) having average pore sizes ranging form 30–60 $\mu$m were composited with a permselective PAN/PVC membrane by a dipcoating procedure. The foam rods were dipcoated with PAN/PVC dissolved in DMSO solvent (12.5% polymer w/w in DMSO), and phase inverted to form the membrane by immersion in a non-solvent water bath. Foam rod devices with PAN/PVC outer membrane coatings were sterilized by soaking in ethanol. The foam rods were then coated with poly-ornithine to improve cell adhesion to the foam material prior to infusing devices with cells.

In this experiment neural stem cells derived from mice (see, e.g., Richards et al., *Proc. Natl. Acad. Sci, USA.* 89: 8591–95 (1992)) were encapsulated. Cells were loaded into the above foam rod/membrane composite devices and held in vitro. Cell viability and distribution were examined after one week and three weeks by staining with fluorescein diacetatelpropidium iodide (FDA/PI) and found to be good to excellent (70–90%). In contrast, murine stem cell viability in Vitrogen™ hydrogel matrix devices was significantly lower (approx. 50%).

Example 6
C₂C₁₂ Myoblast Cells Encapsulated within Hollow Fiber Membranes with Polyurethane Foam Matrix In this experiment, a polyurethane foam scaffold was fabricated in the lumen of a pre-formed 0.2 μm polyethersulfone hollow fiber membrane (AG Tech, Mass.). A polyurethane foam scaffold was formed within the hollow fiber membrane using a polyurethane prepolymer (Hypol™, Hampshire Chemical Corp., Lexington, Mass.). The foam was prepared according to the manufacturer's instructions. Briefly, the foam was formed through the reaction of a linear OH-terminated polymer with an excess of diisocyanate resulting in an isocyanate-terminated polymer rich in polyoxyethylene. When reacted with an aqueous additive this then formed an insoluble biocompatible elastomer. The first step in the reaction between the polyisocyanate and the polyhydroxy compound results in the unstable formation of a carbamic acid. This acid then breaks down into amine and $CO_2$. As the reaction continues, the amine and isocyanate chains form urea groups. The $CO_2$ gas produced forms the desired open-cell foam structures of the matrix materials. A surfactant may be added to the aqueous solution to facilitate pore formation. In this example, the surfactant supplied by the manufacturer was used.

Once the foam material was polymerized within the hollow fiber membranes, we cut the membrane and formed encapsulation devices by the addition of a septal loading hub (as described in Example 1).

$C_2C_{12}$ myoblast cells (20 μL of a 20,000 cell/L suspension) were loaded with a Hamilton syringe into hollow fiber membrane devices with polyurethane foam scaffold in the lumen. The devices were immediately cut open and stained with MTT cell viability stain to visualize viability and cell distribution. Cell distribution was found to be excellent along a length of 1.5 cm. This indicated that the pore structure formed was sufficiently interconnected to allow infusion of cells along the length of the hollow fiber membrane device.

Example 7
Additional Cells Encapsulated within a Foam Matrix

Additional cell encapsulation devices were fabricated according to the procedures of Example 1 with additional cell types, secreting various biologically active molecules.

$C_2C_{12}$ myoblast cells were transformed to produce ciliary neurotrophic factor (CNTF), neurotrophin 4/5 (NT-4/5), both CNTF and NT-4/5, and glial derived neurotrophic factor (GDNF), using methods substantially as described in Example 3. Hollow fiber devices with a PVA foam matrix core were fabricated containing such cells in the manner described in Example 1. The devices were implanted into pigs and sheep. Overall, the devices showed good cell viability and biologically active molecule output, and when compared to counterpart cell encapsulation devices (a comparison was not performed for all experiments), the foam scaffold devices performed better (on these criteria) than counterpart devices with a liquid core or a collagen core.

Chinese hamster ovary (CHO) cells that had been engineered to secrete NT4/5 in hollow fiber devices with a PVA foam matrix core also were encapsulated. After one month in vitro, these devices showed excellent viability in defined media. The PVA foam core controlled cell proliferation 2- to 3-fold better than agarose or vitrogen. We repeated this in vitro study using NIH 3T3 fibroblasts and found good cell viability in serum containing media We also repeated this in vitro study using Hs27 human foreskin fibroblasts. The preliminary data indicate a 2-fold greater cell viability than counterpart devices with a vitrogen matrix core.

Additional embodiments will be suggested by the foregoing disclosure to those skilled in this art. All such obvious embodiments are intended to be encompassed by the concept of this invention as defined in the following claims.

We claim:

1. A method of manufacturing an implantable, biocompatible cell encapsulation device comprising:
   (a) forming a jacket comprising a permeable biocompatible material;
   (b) loading the jacket with a core comprising a reticulate foam scaffold having interconnected pores, the pore density of the foam varying between 20%–90%, the core further comprising a population of living mammalian cells dispersed in the pores:
   (c) sealing the jacket;
wherein the jacket provides at least one permeable membrane surface which permits passage of biologically active substances across said membrane while preventing passage of mammalian cells thereacross.

2. The method of claim 1, wherein the foam scaffold is a thermoplastic or a thermoplastic elastomer.

3. The method of claim 1, wherein the foam scaffold is formed from a material selected from the group consisting of polysulfone, polyethersulfone, polyurethane, and polyvinyl alcohol.

4. The method of claim 1, wherein the void volume of the foam scaffold is between 20 to 90%.

5. The method of claim 1, wherein the foam scaffold has been coated with an extracellular matrix adhesion molecule or adhesion peptide fragment thereof.

6. The method of claim 1, wherein the foam scaffold is coated with one or more extracellular matrix molecules from the group consisting of collagen, laminin, vitronectin, polyornithine, fibronectin, elastin, glycosaminoglycans and proteoglycans.

7. The method of claim 1, wherein at least a portion of the foam scaffold is exposed to a non-permissive material that inhibits mammalian cell proliferation or migration.

8. The method of claim 1, wherein the loading of the jacket in step (b) further comprises the steps of:
   (i) forming a core within the jacket, the core comprising a reticulate foam scaffold having interconnected pores, the pore density of the foam varying between 20%–90%; and
   (ii) loading the core with a population of living mammalian cells.

* * * * *